United States Patent [19]

Wu et al.

[11] 4,204,527

[45] May 27, 1980

[54] DISPOSABLE URETHRAL CATHETER ASSEMBLY

[75] Inventors: Yeongchi Wu, Darien; Christopher A. Nowacki, Des Plaines, both of Ill.

[73] Assignee: Rehabilitation Institute of Chicago, Chicago, Ill.

[21] Appl. No.: 831,701

[22] Filed: Sep. 12, 1977

[51] Int. Cl.² ............................................. A61M 3/00
[52] U.S. Cl. ................................... 128/762; 128/294; 128/349 R; 128/767
[58] Field of Search ............... 128/2 F, 294, 295, 275, 128/276, 227, 349 R, DIG. 9, DIG. 24; 4/10; 206/571

[56] References Cited

U.S. PATENT DOCUMENTS

| | | | |
|---|---|---|---|
| 2,784,716 | 3/1957 | Broman | 128/227 |
| 2,856,932 | 10/1958 | Griffitts | 128/294 |
| 2,863,453 | 12/1958 | Gewecke | 128/227 |
| 2,883,985 | 4/1959 | Evans | 128/295 |
| 3,175,553 | 3/1965 | Mattson | 128/2 |
| 3,228,444 | 1/1966 | Weber et al. | 128/2 F X |
| 3,312,221 | 4/1967 | Overment | 128/275 |
| 3,335,714 | 8/1967 | Giesy | 128/2 |
| 3,336,926 | 8/1967 | Gresham | 128/295 |
| 3,364,932 | 1/1968 | Beach | 128/295 |
| 3,403,410 | 10/1968 | Benzel et al. | 4/110 |
| 3,526,227 | 9/1970 | Appelbaum | 128/295 |
| 3,724,461 | 4/1973 | Eisenberg | 128/227 |
| 3,740,770 | 6/1973 | Villari | 128/295 |
| 3,742,953 | 7/1973 | Lee | 128/295 |
| 3,743,532 | 10/1969 | Eisenberg | 128/227 |
| 3,749,096 | 7/1973 | Donaldson | 128/293 |
| 3,762,399 | 10/1973 | Riedell | 128/2 F |
| 3,835,857 | 9/1974 | Rogers et al. | 128/295 |
| 3,878,571 | 4/1975 | Seeley | 4/110 |
| 3,888,236 | 6/1975 | Marx | 128/2 F |
| 3,921,634 | 11/1975 | Mather et al. | 128/227 |

FOREIGN PATENT DOCUMENTS

| | | | |
|---|---|---|---|
| 471130 | 8/1974 | Australia | 128/295 |
| 1197910 | 7/1970 | United Kingdom | 128/276 |
| 1199498 | 7/1970 | United Kingdom | 128/2 F |
| 1232763 | 5/1971 | United Kingdom | 128/295 |

Primary Examiner—E. H. Eickholt
Attorney, Agent, or Firm—Trexler, Wolters, Bushnell & Fosse, Ltd.

[57] ABSTRACT

A disposable urethral catheter assembly includes a flexible bag in which are defined a number of chambers. In an upper chamber, a catheter is contained in a sterile environment. When the catheter is inserted into the urethra, the fluid flows into the bag and into a lower sample chamber, excess fluid being collected in the upper chamber. After catheter use, a cannula plug seals a first barrier between the upper and lower chamber and thus isolates the sample in the lower chamber. The upper chamber, its contents and the catheter are discarded, and the lower sample chamber and its contents are sent to a laboratory for analysis and culture.

23 Claims, 10 Drawing Figures

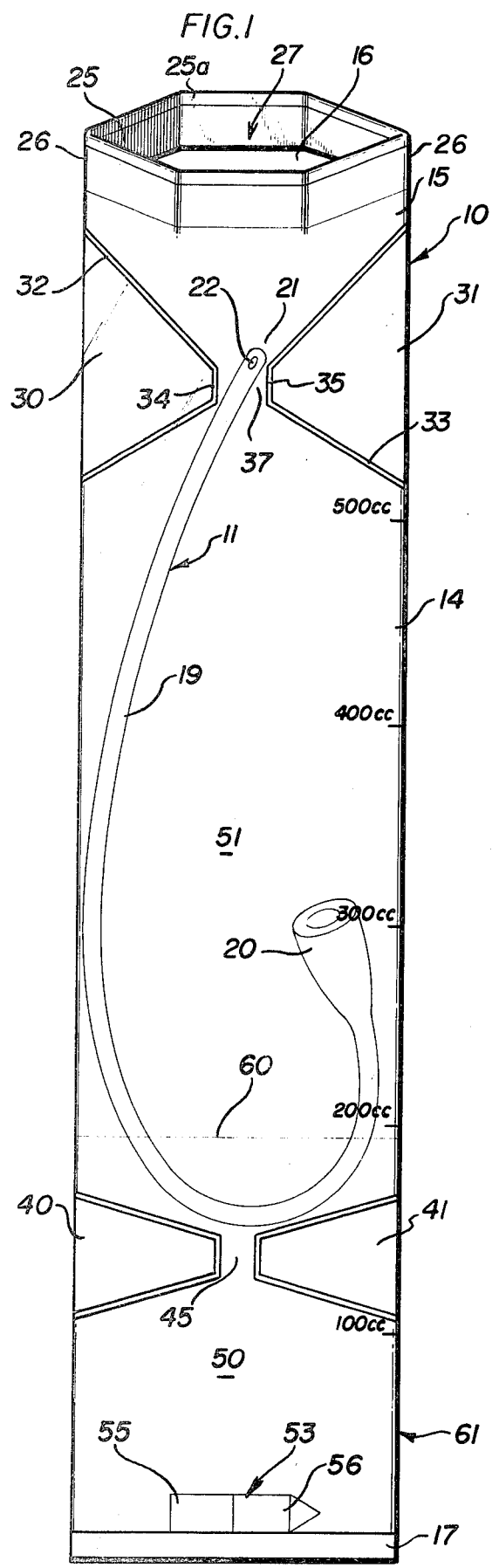
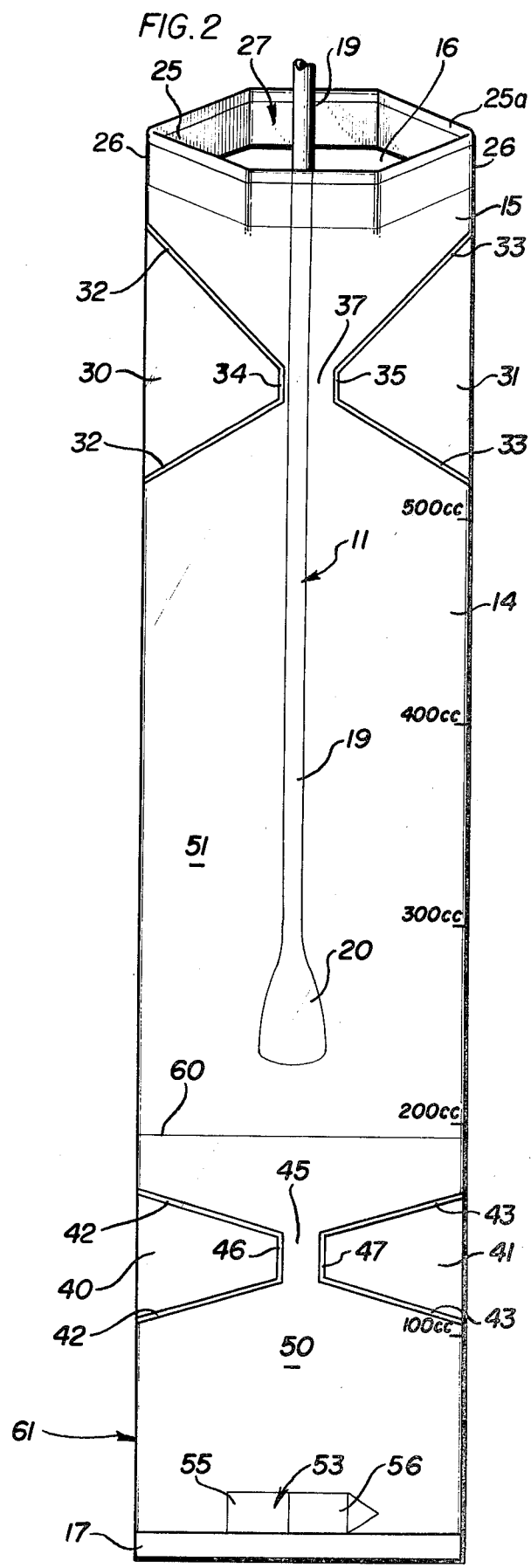

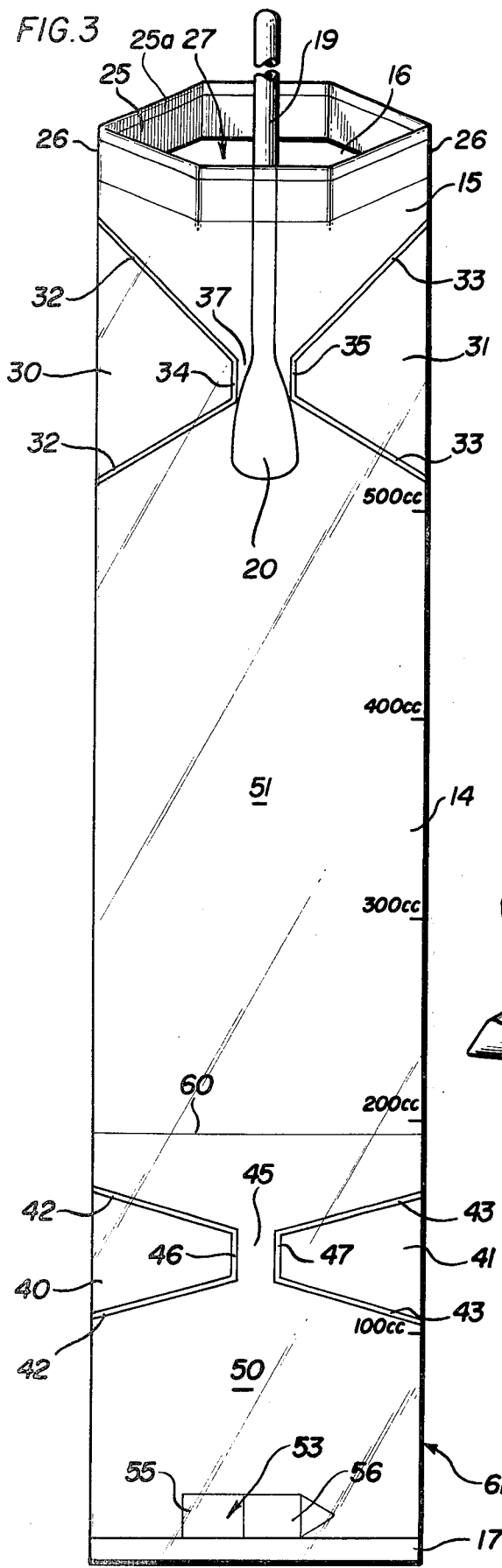
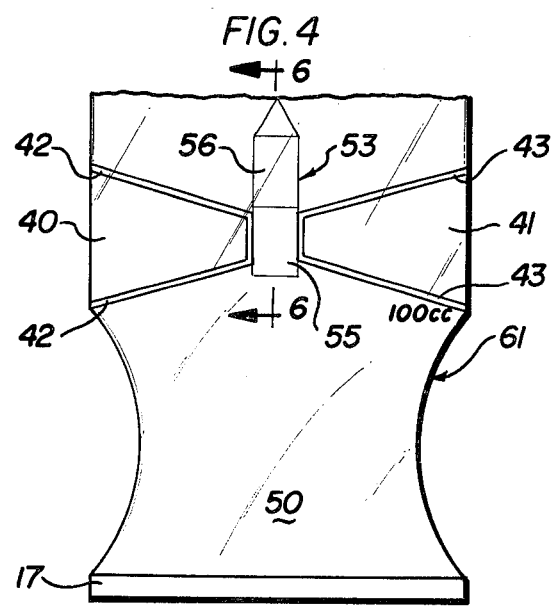
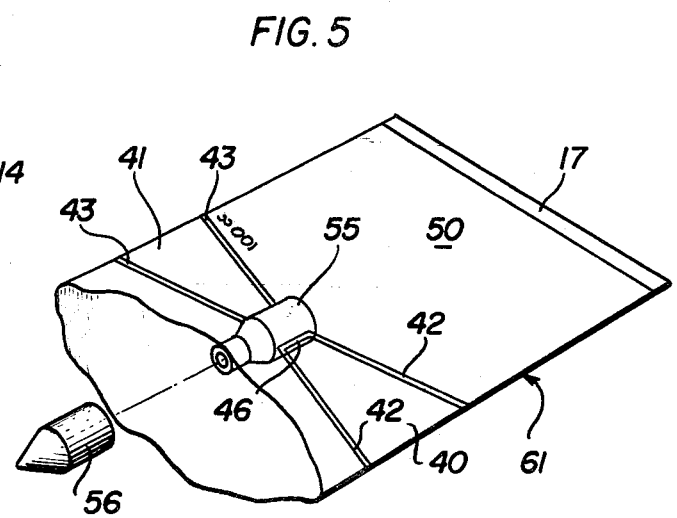
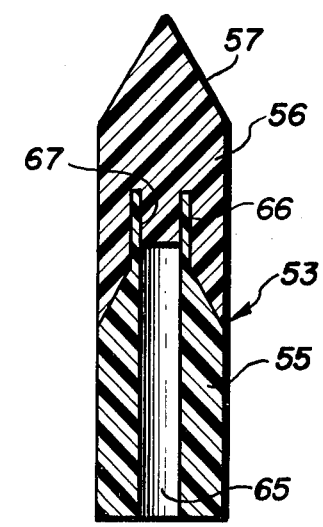

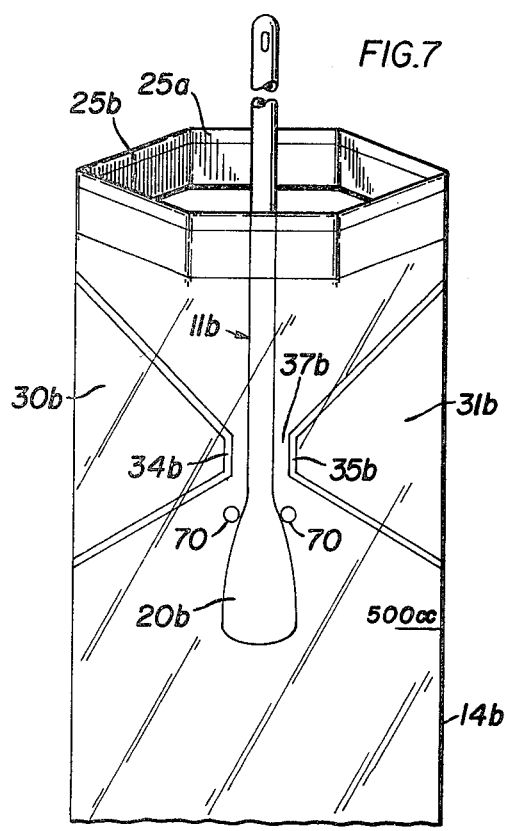
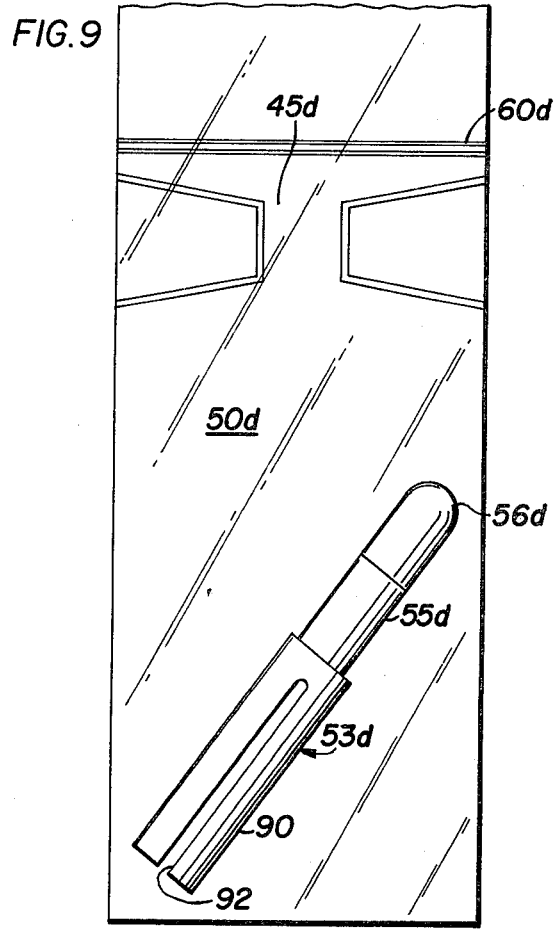
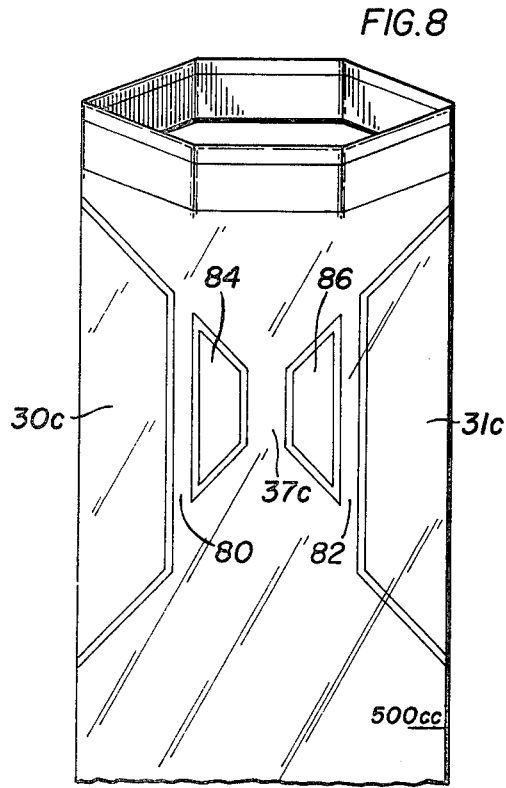
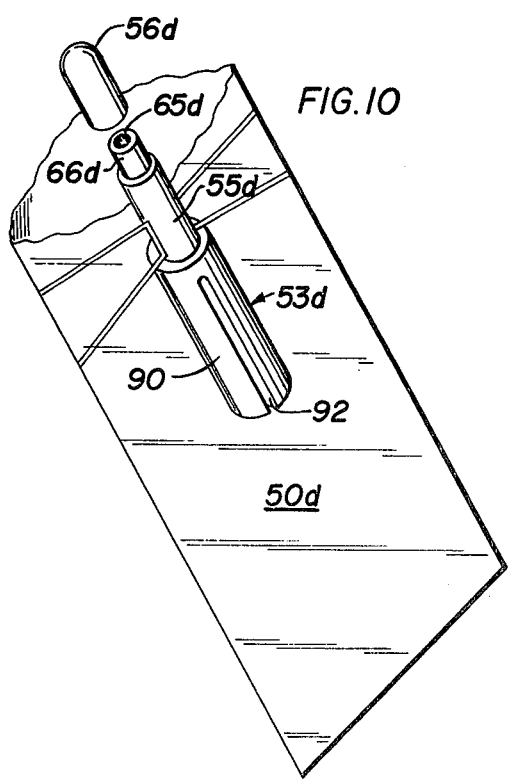

DISPOSABLE URETHRAL CATHETER ASSEMBLY

BACKGROUND OF THE INVENTION

This invention relates generally to fluid collectors for use with catheters and related apparatus, and more particularly concerns a catheter fluid collector device which more or less automatically isolates a fluid sample for later laboratory study, including urinalysis and culture and sensitivity tests.

Many victims of paralysis are unable to voluntarily evacuate their bladder. These persons must be catheterized periodically in order to remove accumulating body waste fluids.

A number of non-surgical and semi-surgical techniques and related devices have been offered to perform this catheterization. For male patients this procedure in general involves aseptically preparing the penis, and then inserting a catheter into the urethra, while maintaining sterile technique, until the eye of the catheter reaches and communicates with the bladder. Urine then flows through the catheter and can be directed into a collection container or disposal device.

If a urine specimen is required for medical analysis, the urine flow from the catheter is directed into a specimen collection container until an adequate sample is collected; remaining portions of the urine flow are then directed back into the disposal structure. When the bladder has been emptied and the procedure completed, the catheter is removed and disposed of, and the specimen container is sealed and sent to a laboratory for microbiological and biochemical studies.

At least some of these techniques and their associated implements offer the dangers of urethra contamination during procedure preparation, catheter contamination during handling, and specimen contamination during speciment container filling, sealing and emptying. Many of the techniques and associated apparatus must be performed in a semi-surgical setting; they cannot be conveniently performed by the patient himself while he is alone and in a semi-private washroom or other location.

Additionally, when collector bags or receptacles are provided, some catheterization apparatus permit inadvertent removal of the catheter from the collector, thus presenting the possibility of accidental spillage and attendant mess. Such an occurrence can cause discomfort and even humiliation to the patient.

It is accordingly the general object of the present invention to provide a urine collector which is handy and safe to use, and which more or less automatically containerizes a urine sample for laboratory analysis.

It is a more specific object of the invention to provide a urine collector and catheter device which minimizes the danger of catheter contamination during catheter insertion into the urethra. An associated object is to provide such a collector and catheter which encourages and maximizes the maintenance of sterile technique. An ancillary object is to provide such a collector and catheter which permits catheter insertion without the catheter being directly touched or handled at any time.

Another object of the invention is to provide a urine collector and catheter which minimizes the risk of urine sample contamination from outside sources. A related object is to provide such a collector and catheter which more or less automatically segregates or defines and encapsulates or containerizes a urine sample. A related object is to provide such a device in which the sealed urine sample is contained in a handy chamber, and which can be poured and otherwise manipulated in the laboratory with relative ease.

Yet another object is to provide a collector and a catheter which can be used even by the patient himself when he is alone in a washroom or a relatively private area.

A further object of the invention is to provide such a collector and catheter which can be manufactured, packaged, and commercially offered at an attractive cost.

Still another object is to provide such a collector and catheter which can be used with relative ease even by relatively inexperienced personnel. An associated object is to provide such a collector and a catheter which can be used by the patient himself with a minimum of instruction to thereby reduce the professional time and final medical expense.

Other objects and advantages of the invention will become apparent upon reading the following detailed description and upon reference to the drawings. Throughout the drawings, like reference numerals refer to like parts.

BRIEF DESCRIPTION OF THE DRAWINGS

FIG. 1 is an elevational view of the novel collector and catheter as they appear when ready for use;

FIG. 2 is an elevational view similar to FIG. 1 showing the catheter and collector as they can appear when the catheter is being inserted into the urethra;

FIG. 3 is an elevational view similar to FIGS. 1 and 2 and showing the collector and catheter as they can appear when the catheter has been relatively fully inserted and is about to deliver a quantity of fluid to the collector.

FIG. 4 is an elevational view of a collector first chamber which has been filled with fluid and sealed for removal to a laboratory for analysis;

FIG. 5 is a perspective view of the collector first chamber and associated cannula plug;

FIG. 6 is a sectional view of the cannula plug taken substantially in the plane of line 6—6 in FIG. 4;

FIG. 7 is an elevational view in partial section of a second embodiment of the collector bag;

FIG. 8 is an elevational view in partial section of a further embodiment of the collector bag;

FIG. 9 is an elevational view in partial section of a collector first chamber with a modified cannula plug; and FIG. 10 is a perspective view of a collector first chamber which has been filled with fluid and with the modified cannula plug in fluid delivering position.

DETAILED DESCRIPTION

While the invention will be described in connection with a preferred embodiment and procedure, it will be understood that it is not intended to limit the invention to this embodiment or procedure. On the contrary, it is intended to cover all alternatives, modifications and equivalents as may be included within the spirit and scope of the invention and defined by the appended claims. For example, this collector device and procedure can be used, with suitable minor modifications, by female as well as male patients.

Turning first to FIG. 1, there is shown the novel collector 10 and catheter 11 embodying the present invention. Here the collector takes the form of a transparent flexible bag 14 made of a suitable polymeric film such as any of the apropriate polyolefins, polystyrenes or the like. The bag can be of an elongated form, as illustrated, and is defined by two folded or otherwise opposed material layer films 15 and 16 sealed at a bottom 17 and may also be sealed at the top 25a with a suitable tear seal. Such sealing of top 25a can be used in the event the collector is not packaged in a secondary sterile container or envelope. It is contemplated that the bag interior will be rendered sterile by appropriate operations during manufacture.

The catheter 11 can be considered to comprise an elongated hollow tube 19 terminating at one end in an enlarged or bulbous discharge end 20. At an opposite tip 21, an eye or perforation 22 communicates with the hollow tube interior, as is well known in the art of urethra catheters. The catheter, too, is rendered sterile during manufacturing.

After manufacturing production and prior to use, the catheter 11 is carried in a sterile environment. To this end, the bag 14 is provided with a closure top 25. If desired, a resilient member within the closure top 25 can be biased into an open position from its normally closed position by squeezing opposite edges 26 toward each other to provide an irregular, hollow, polygonal opening and chamber 27 for accommodating the head of a male penis. This top chamber 27 is at least partly defined by two upper chevrons 30 and 31 formed within and upon the bag, as by heat sealing narrow bands 32 and 33 of one bag side 15 against the opposite bag side 16.

In use, the urethra orifice and head of the penis is asepticized. The bag top 25 is then opened, thereby exposing and forming the top chamber 27. A suitable lubricant is added to top chamber 27 and the penis glans is inserted into chamber 27 until it contacts chevrons 30 and 31 thereby orienting and aligning the urethra with the opening 37. The bag 14 and catheter 11 are then manipulated so as to extend the catheter 11 out from the top of the bag, as illustrated in FIG. 2. In accordance with one aspect of the invention, this procedure eliminates the need for directly touching the catheter 11, for the bag opening 27 is adapted to be brought over the penis head. Since the interior of the opening 27 is aseptic, catheterization procedure sterility is encouraged.

It will be noted that these upper chevrons 30 and 31 extend toward one another, but terminate at truncations 34 and 35, respectively, which define a restricted opening 37 through which the catheter tube 19 extends. To discourage inadvertent catheter removal in accordance with another aspect of the invention, the opening 37 is reduced in size relative to the enlarged catheter bulbous end 20 whereby end 20 cannot be inadvertently pulled through, as particularly illustrated in FIG. 3. When male patients use the novel device, the catheter can be gripped through the bag with the forefinger and thumb of one hand while the penis is held against the chevrons 30 and 31 inside the bag top cavity 27. The patient or user eases the catheter tube 19 into the urethra orifice and into the urethra itself with succeeding gripping and releasing motions, allowing the plastic bag 14 to relax into its original position after each movement. In this way, the catheter is inserted into the urethra until the catheter tube opening 22 enters the bladder and urine begins flowing into the bag. Urine flow is permitted until a substantial portion of the bladder has been evacuated. When catherization has been completed, or when the maximum acceptable volume has been received in the bag, the patient or user removes the catheter and bag in one outward motion.

In accordance with yet another aspect of the invention, a urine sample of convenient volume for laboratory analysis is more or less automatically collected by this device and procedure. To this end, two lower chevrons 40 and 41 are formed within and upon the bag, as by heat sealing the bag sides 15 and 16 to one another along outwardly diverging lines 42 and 43 respectively. A relatively narrow opening 45 is defined between two opposed heat sealed lines 46 and 47, and through this opening 45 a predetermined quantity of fluid can flow into a specimen reservoir, here comprising a lower or first chamber 50. When the first chamber is filled, additional fluid accumulates in a relatively upper or second chamber 51. The total volume of fluid material collected can be determined with reasonable accuracy by a volumetric measurement scale marked upon the bag when the bag is held in a vertical position, as indicated in FIGS. 1 through 3.

Lying within the first chamber 50 is a cannula plug 53 formed to fit within and seal the restricted inter-chamber opening 45, as shown in FIG. 4, thereby defining or sealing off a urine sample in the lower or first chamber 52 for laboratory analysis. In a preferred embodiment, this cannula plug 53 is formed of air-entrained plastic or other suitably inert but lightweight material which causes the plug to float with the tip in the up position toward the opening 45. This plug 53 can be considered to include a base 55 and a trocar-like cap 56 defined by a tapered point 57. Because the plug 53, which is lighter at the tip part 56 than at the base part 55, floats, it preliminarily moves toward the opening 45 as the first chamber 50 is filled, thereby minimizing final plug insertion and chamber sealing trouble and effort.

After the plug 53 has been inserted in the opening 45, the top or second chamber 51, the catheter 11, and other portions of the device can be discarded, in further accordance with the invention. To do this, the entire device 10 is preferably removed to a disposal area, where the fluid in the second or top chamber 51 is emptied. The patient or attendant then removes the catheter 11 and top portion of the bag 14, as by tearing or cutting along a convenient sever line 60 which can be marked upon the bag; or with removal of the catheter, the patient empties the urine and seals the whole bag from the opener 25 by folding it several times toward the lower portion 61. The lower portion 61 of the device, including the filled and sealed first chamber 50, can then be transmitted to the laboratory for urine analysis and culture, sensitivity tests together with desired identifying data, such as the patient's name and any hospital room number.

In the laboratory, a laboratory technician removes the trocar top cap portion 56 from the base 55 of the cannula plug 53, as illustrated particularly in FIG. 5. The plug base portion 55 is provided with a bore 65 which is exposed by removal of cap 56. In accordance with another aspect of the invention, urine from the specimen chamber 50 can thus be conveniently directed to analysis or test equipment. To insure good base-cap fit, the base 55 can be provided with an extended annular nipple 66, and a plug 67 extends from the cap 56 into the nipple 66 for a convenient but short distance, as illustrated particularly in FIG. 6. After the fluid sample is dispensed and tests have been completed, the device lower portion 61 and any unused fluid can also be discarded, thereby eliminating any need to undertake costly re-sterilization procedures.

Referring now to FIG. 7, wherein similar numerals are utilized to designate similar parts with the addition of the suffix "b". The bag 14b includes a top seal 25a and a closure top 25b plus chevrons 30b and 31b of the same general configuration in the first embodiment. Each of the chevrons 30b and 31b have truncated portions 34b and 35b respectively and form an opening 37b. It was found in the use of the primary embodiment that occasionally the bulbous end 20b of the catheter 11b could block the opening 37b and thereby prevent the flow of air out of the bag as it is being filled. To overcome this, a pair of spaced heat sealed points 70 are provided in axial spaced relation relative to opening 37b. These points 70 space the bulbous end 20b of catheter 11b and permit the escape of entrapped air from within the bag.

The collector shown in FIG. 8 is substantially similar to the other embodiments with the addition of two channels 80 and 82 in the chevrons 30c and 31c, respectively. The relatively lower edges of the truncated segments 84 and 86 are axially displaced from the lower edges of chevrons 30c and 31c. This prevents any attempts to force a catheter, not shown, into the channels 80 or 82 but rather directs such a catheter into the centrally located opening 37c for insertion into the urethra.

FIGS. 9 and 10 disclose a modified plug 53d for sealing the lower or first chamber 50d. The bag 14d has a predetermined width and the plug 53d has an overall length greater than said predetermined width whereby the plug 53d cannot become inadvertently inverted when it is utilized to seal the opening 45d at the top of lower chamber 50d.

Plug 53d includes a base 55d, a through bore 65d, an extended annular nipple 66d and a cap portion 56d. Plug 53d also includes a hollow lower extension 90 having a transverse slot 92 for assisting in the evacuation of a test sample from lower chamber 50d. It should be noted that extension 90 has a diameter greater than opening 45d thereby insuring proper insertion of base 55d into opening 45d to thereby expose cap 56d for removal to permit evacuation of the test sample.

I claim:

1. A fluid collector comprising a urethra catheter for delivering a quantity of liquid from a human body, and a flexible bag containing the catheter prior to catheter use, the bag including first barrier means defining at least a first chamber capable of containing a predetermined volume of liquid and a second chamber capable of containing the liquid delivered from the body in excess of the liquid deposited in the first chamber, the collector further including a cannula plug member for fully sealing the first chamber from the second chamber after the first chamber has been filled.

2. A fluid collector according to claim 1 wherein said bag is formed of a transparent flexible polymeric film.

3. A fluid collector according to claim 1 wherein said first barrier means includes two opposed chevron formations formed in and on said bag.

4. A fluid collector according to claim 3 wherein said chevron formations include a chevron defining line portion of said bag heat sealed to an adjacent but opposed portion of the bag.

5. A fluid collector according to claim 4 wherein said chevrons take the form of opposed trapezoids.

6. A fluid collector according to claim 1 wherein said cannula plug member comprises a base and a trocar cap adapted to guide the cannula plug member into sealing engagement with said barrier means.

7. A fluid collector according to claim 6 wherein said cannula plug base includes pour means for retaining the trocar cap upon the base, and for pouring the liquid from said first chamber after cap removal.

8. A fluid collector according to claim 1 including second barrier means separating said second chamber at least partially from an adjacent portion of said bag, said second barrier means having a central passageway adapted to permit passage therethrough of at least part of said catheter.

9. A fluid collector according to claim 8 wherein said catheter is equipped with stop means preventing complete withdrawal of the catheter from the second chamber.

10. A fluid collector according to claim 8 wherein said catheter stop means comprises an enlarged catheter end for abutment against said second barrier means when withdrawal of said catheter from said chamber is attempted.

11. A fluid collector comprising, in combination, a volume-calibrated, internally sterile bag adapted to contain a urethra catheter therein, the lower portion of the bag including heat sealed chevrons forming a fluid specimen reservoir of predetermined volume, a cannula plug contained within said specimen reservoir for insertion between the chevrons to seal the specimen reservoir from remaining portions of the bag, the bag further including a second set of heat sealed opposed chevrons near the top of the bag defining a channel through which the catheter is extended during catheterization and further defining, at least in part, a restricted chamber at the bag top for accepting a male penis.

12. A fluid collector comprising a urethra catheter and an elongated flexible container having, at its top, a stiffened resilient cuff normally biased into a closed position, a pair of seal lines defining a restricted top chamber at the bag top, an upper chamber housing the urethra catheter, a heat sealed restrictive opening defining the bottom of said upper chamber and the top of a lower chamber, and a cannula plug for closing the upper chamber from the lower chamber.

13. A fluid collector according to claim 12 wherein said cannula plug includes a trocar cap, and a base defining a bore, the emplaced cap sealing the bore from fluid flow therethrough.

14. A fluid collector bag comprising, in combination, a flexible film defining two opposed bag sides, and first barrier means defining at least a first chamber capable of containing a predetermined volume of fluid and a second chamber capable of containing liquid in excess of the liquid deposited in the first chamber, the first barrier means also defining a restricted opening and plug means initially positioned in said first chamber cooperating with said restricted opening for selectively sealing the first chamber from the second chamber after the first chamber has been filled.

15. A fluid collector bag according to claim 14 including closure means at a bag top capable of being opened to define a chamber for accommodating the head of a male penis.

16. A fluid collector according to claim 15 wherein closure means includes a resilient member normally biased into a closed position having two sides in relative abutment and, when opened, defining a hollow polygonal opening.

17. A fluid collector according to claim 9 wherein said stop means includes at least a pair of laterally spaced abutments axially spaced from said second barrier means and with the space between said abutments being aligned with said second passageway and adapted to provide an air passageway for escape of entrapped air in said collector.

18. A fluid collector according to claim 11 wherein said second set of opposed chevrons includes secondary channel means adapted to permit escape of entrapped air during filling of said collector.

19. A fluid collector according to claim 18 wherein said chevrons each include at least a pair of truncated trapezoids laterally spaced from one another to form a large centrally disposed channel adapted to accept said catheter for passage therethrough and at least one secondary channel for escape of entrapped air.

20. A fluid collector according to claim 19 wherein the centrally disposed truncated trapezoids forming the centrally disposed channel have one edge facing the specimen reservoir which is axially offset from the adjacent edge of the laterally adjacent truncated trapezoid.

21. A fluid collector according to claim 13 wherein said container lower chamber has a predetermined width, said cannula plug including said base, said cap and an extension to said base have an overall length greater than said predetermined width whereby said plug cannot be inadvertently inverted in said lower chamber but rather insures positionment of said cap in said restricted opening.

22. A fluid collector according to claim 21 wherein said extension is diametrally larger than said restricted opening to further insure proper orientation of said plug.

23. A fluid collector according to claim 22 wherein said extension is slotted through a substantial portion of its length, said slot communicating with said bore and adapted to facilitate drainage of said lower chamber.

* * * * *